US009034586B2

(12) United States Patent
Sanuki et al.

(10) Patent No.: US 9,034,586 B2
(45) Date of Patent: *May 19, 2015

(54) METHOD OF DETECTING PANCREATIC DISEASE AND PANCREAS TESTING KIT

(71) Applicant: OYLMPUS CORPORATION, Tokyo (JP)

(72) Inventors: Hiromi Sanuki, Tokyo (JP); Rie Kataoka, Tokyo (JP); Nao Moriya, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/043,267

(22) Filed: Oct. 1, 2013

(65) Prior Publication Data

US 2014/0030823 A1  Jan. 30, 2014

Related U.S. Application Data

(63) Continuation of application No. PCT/JP2012/059222, filed on Apr. 4, 2012.

(30) Foreign Application Priority Data

Apr. 5, 2011  (JP) ................................. 2011-083910

(51) Int. Cl.
| G01N 31/00 | (2006.01) |
| G01N 33/53 | (2006.01) |
| G01N 21/78 | (2006.01) |
| G01N 33/574 | (2006.01) |
| G01N 33/487 | (2006.01) |
| G01N 33/68 | (2006.01) |
| C12Q 1/68 | (2006.01) |
| A61B 10/00 | (2006.01) |
| A61B 5/00 | (2006.01) |

(52) U.S. Cl.
CPC ........ *G01N 21/78* (2013.01); *C12Q 1/68* (2013.01); *A61B 10/0045* (2013.01); *G01N 33/57438* (2013.01); *A61B 5/4216* (2013.01); *G01N 33/487* (2013.01); *G01N 33/6893* (2013.01); *G01N 2800/067* (2013.01)

(58) Field of Classification Search
CPC . G01N 33/487; G01N 33/57438; C12Q 1/68; A61B 5/4216; A61B 10/0045
See application file for complete search history.

(56) References Cited

U.S. PATENT DOCUMENTS

| 5,651,769 | A | 7/1997 | Waxman et al. |
| 6,498,143 | B1 | 12/2002 | Beck et al. |
| 8,529,547 | B2 * | 9/2013 | Sanuki et al. ................ 604/540 |
| 8,586,384 | B2 * | 11/2013 | Moriya et al. ............... 436/514 |
| 2002/0135766 | A1 | 9/2002 | Darrow et al. |
| 2007/0015156 | A1 | 1/2007 | Goggins |
| 2007/0213631 | A1 | 9/2007 | Kondo et al. |
| 2007/0286858 | A1 | 12/2007 | Clancy et al. |

FOREIGN PATENT DOCUMENTS

| CN | 1297922 A | 6/2001 |
| CN | 1339108 A | 3/2002 |
| CN | 101405300 A | 4/2009 |
| CN | 101903775 A | 12/2010 |
| JP | 2009-529920 A | 8/2009 |
| WO | WO 2010/047448 A1 | 4/2010 |

OTHER PUBLICATIONS

Deng et al. American Journal of Clinical Pathology, 2008, vol. 129, pp. 81-88.*
Paulo et al. Electrophoresis, 2010, vol. 31, pp. 2377-2387.*
Paulo et al. Electrophoresis, Jul. 2010, vol. 31, No. 14, pp. 2377-2387.*
English Abstract only of WO 2007/109747 A2, dated Sep. 27, 2007.
Paulo, Joao A. et al., "Optimized sample preparation of endoscopic collected pancreatic fluid for SDS-PAGE analysis", Electrophoresis (2010), vol. 31, pp. 2377-2387.
Ohuchida, Kenoki et al. "S100P Is an Early Developmental Marker of Pancreatic Carcinogenesis", Clinical Cancer Research (2006), vol. 12, pp. 5411-5416.
Gronborg, Mads et al., "Comprehensive Proteomic Analysis of Human Pancreatic Juice", Journal of Proteome (2004), vol. 3, pp. 1042-1055.
International Search Report dated May 15, 2012 issued in PCT/JP2012/059222.
Noh, K.W., et al., "Do Cytokine Concentrations in Pancreatic Juice Predict the Presence of Pancreatic Diseases?" Clincal Gastroenterology and Hepatology, Jun. 2006, 4(6), 782-789.
Matsumoto, S. et al., "Evaluation of Cytology and Tumor Markers of Pure Pancreatic Juice for the Diagnosis of Pancreatic Cancer at Early Stages", Pancreas, Nov. 1994, 9(6), pp. 741-747.
Koopman, J., et al., "Mac-2-Binding Protein is a Diagnostic Marker for Biliary Tract Carcinoma", Cancer; Oct. 1, 2004; 101(7), pp. 1609-1615.

(Continued)

*Primary Examiner* — Lisa Cook

(74) *Attorney, Agent, or Firm* — Scully, Scott, Murphy & Presser, P.C.

(57) ABSTRACT

A pancreatic disease is tested for with high sensitivity even with simple equipment and a simple procedure. Provided is a method of detecting pancreatic disease including detecting a concentration of S100P in at least one of a pancreatic juice and a body fluid containing pancreatic juice collected from a test subject by immunochromatography. Additionally provided is a pancreas testing kit including an immunochromatography device that holds an anti-S100P antibody and a collection vessel that retains a protease inhibitor that inhibits an activity of a protease contained in the pancreatic juice.

6 Claims, 7 Drawing Sheets

(56) References Cited

OTHER PUBLICATIONS

Farnini, R., et al., "CEA Concentration and Cytology in Duodenal Fluid Collected During the Secretin-Pancreozymin Test. Attempt at an Early Diagnosis of Pancreatic Carcinoma by Means of Simple Procedure", Hepatogastronenterology, Jun. 1980, 27(3), pp. 213-216.

Molnar, I.G., et al., "CEA Levels in Fluids Bathing Gastrointestinal Tumors", Gastroenterology, Apr. 1976, 70(4), pp. 513-515.

Osnes, M., "Studies on Recovery and Variation of Pancreatic Juice Obtained by Endoscopic Cannulation of the Main Pancreatic Duct in Man", Scandinavian Journal of Gastroenterology, 1981, 16(1), 39-44, Abstract only.

U.S. Office Action dated Dec. 19, 2012 issued in related U.S. Appl. No. 13/438,907.

Notice of Allowance dated Jul. 12, 2013 issued in related U.S. Appl. No. 13/438,907.

U.S. Office Action dated Dec. 20, 2012 issued in related U.S. Appl. No. 13/439,866.

Notice of Allowance dated May 28, 2013 issued in related U.S. Appl. No. 13/438,866.

Chinese Office Action dated Sep. 10, 2014 received from related Chinese Patent Application No. 201280015866.9.

Xiao G, "Preliminary Study on Pancreatic Tumor Markers in Human Duodenal Fluid and Proteomics", Ph.D. Dissertation from Peking Union Medical College, pp. 94 (Oct. 13, 2010), together with a partial English-language translation.

Chinese Office Action dated Nov. 27, 2014 received from related Chinese Patent Application No. 201280043445.7, together with an English-language translation.

Wandschneider S. et al., "Autoimmune Pancreatic Disease: Preparation of Pancreatic Juice for Proteome Analysis", Electrophoresis 22(20):4383-4390 (2001).

Chinese Office Action dated Jan. 22, 2015 received from related Chinese Patent Application No. 201280015866.9.

Nakata K. et al., "S100P is a Novel Marker to Identify Intraductal Papillary Mucinous Neoplasms", Human Pathology 41(6):824-831 (Jun. 1, 2010).

Extended European Search Report dated Mar. 6, 2015 received from related Application No. 12767863.9.

* cited by examiner

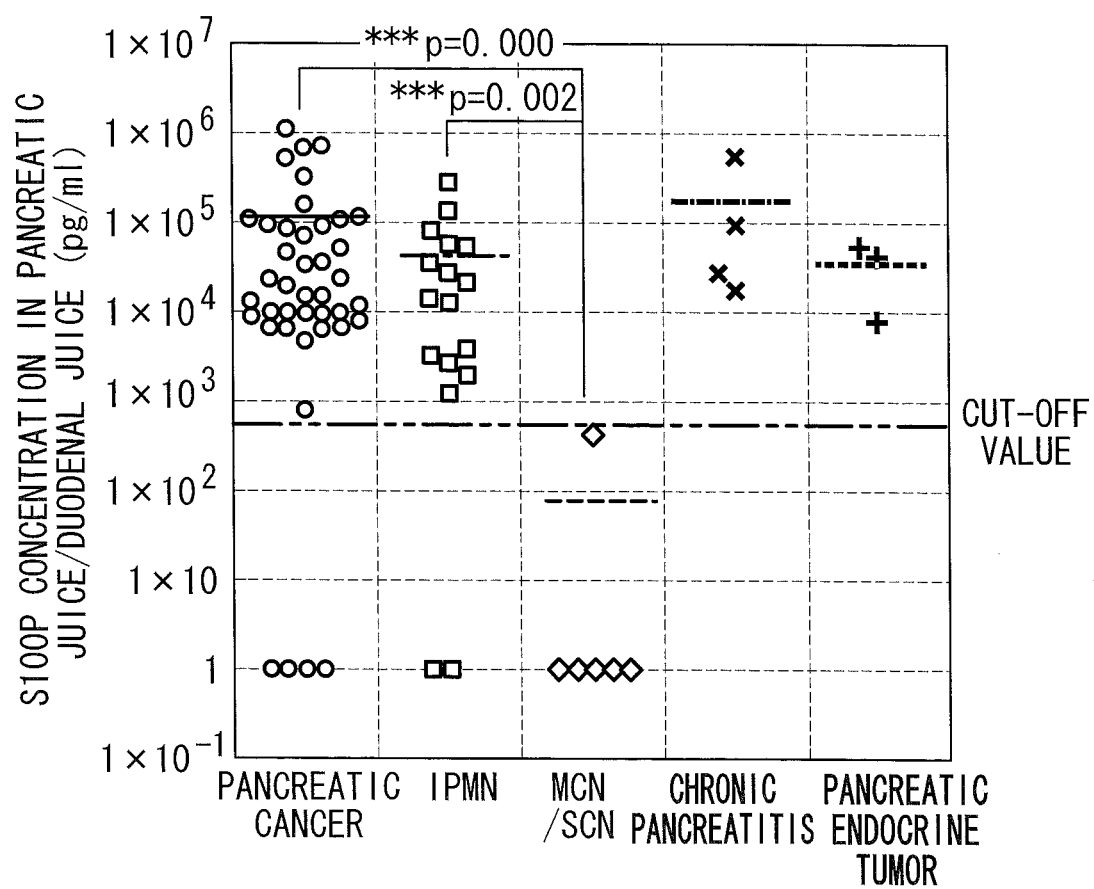

METHOD OF DETECTING PANCREATIC DISEASE AND PANCREAS TESTING KIT

CROSS-REFERENCE TO RELATED APPLICATIONS

This is a continuation of International Application PCT/JP2012/059222, with an international filing date of Apr. 4, 2012, which is hereby incorporated by reference herein in its entirety. This application claims the benefit of Japanese Patent Application No. 2011-083910, the content of which is incorporated herein by reference.

TECHNICAL FIELD

The present invention relates to a method of detecting pancreatic disease and a pancreas testing kit.

BACKGROUND ART

Conventionally, intraductal papillary mucinous neoplasm (IPMN) has attracted attention as a key to the early detection of pancreatic cancer. Pancreatic cancer and IPMN are diagnosed by means of an endoscope examination or biopsy. However, early detection of pancreatic cancer and IPMN based on an endoscope image is difficult, and, in the case of biopsy, the task of collecting tissue from the pancreas itself is difficult. Therefore, it has not been possible to achieve sufficient test precision by using these methods.

On the other hand, with pancreatic cancer and IPMN, it is known that S100P, which is one of the S100 protein families, is overexpressed at a high proportion (for example, see Non Patent Literatures 1 and 2).

CITATION LIST

Non Patent Literature

{NPL 1} Kenoki Ohuchida and 9 others, "S100P Is an Early Developmental Marker of Pancreatic Carcinogenesis", Clinical Cancer Research, Vol. 12, No. 18, pp. 5411-5416, Sep. 15, 2006

{NPL 2} Mads Gronborg and 8 others, "Comprehensive Proteomic Analysis of Human Pancreatic Juice", Journal of Proteome Research, Vol. 3, No. 5, pp. 1042-1055, Sep. 17, 2004

SUMMARY OF INVENTION

A first aspect of the present invention is a method of detecting pancreatic disease, including detecting a concentration of S100P in at least one of a pancreatic juice and a body fluid containing pancreatic juice collected from a test subject by immunochromatography.

A second aspect of the present invention is a pancreas testing kit including an immunochromatography device that holds two types of anti-S100P antibodies that recognize epitopes of S100P that are different from each other, such that the antibodies serve as a first antibody that labels a test substance with a labeling substance and a second antibody that adsorbs the test substance that has formed a complex with the first antibody.

BRIEF DESCRIPTION OF DRAWINGS

FIG. 8 is a graph showing the results obtained by measuring the S100P concentrations in pancreatic juice and duodenal juice for five types of pancreatic disease in Example 3.

DESCRIPTION OF EMBODIMENT

A pancreas testing kit according to an embodiment of the present invention and a method of detecting pancreatic disease employing the pancreas testing kit will be described below with reference to FIGS. 1 to 5.

Figure 1:
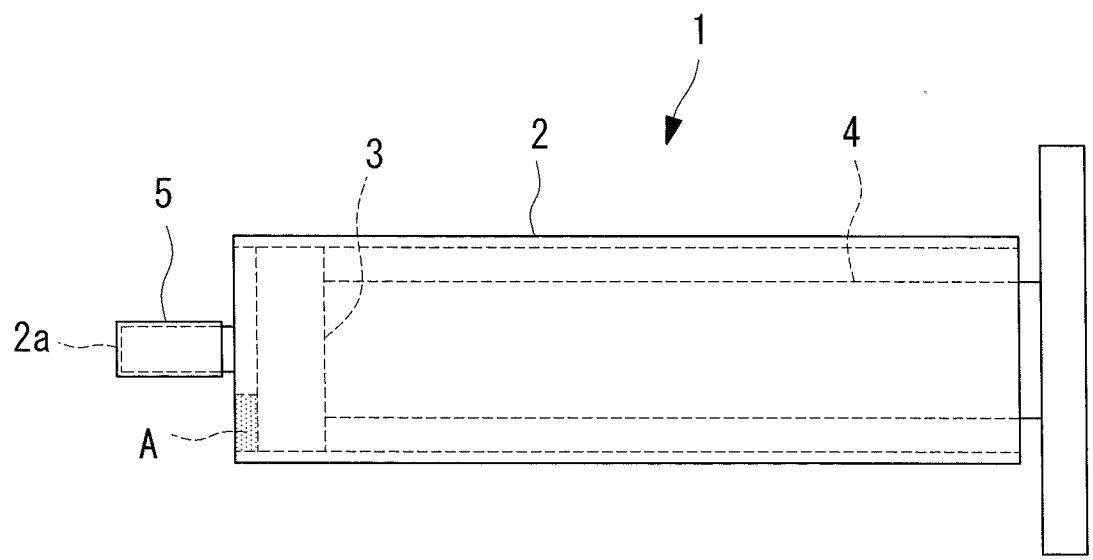
FIG. 1 is an overall configuration diagram of a collection vessel provided in a pancreas testing kit according to an embodiment of the present invention.
Figure 2A:
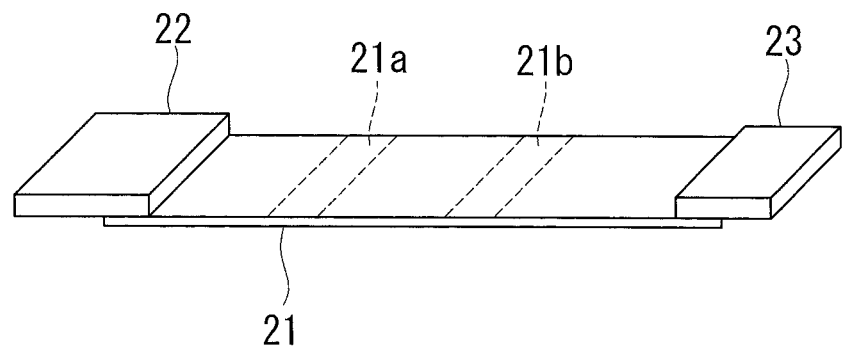
FIG. 2A is a diagram showing the internal configuration of an immunochromatography device provided in the pancreas testing kit according to the embodiment of the present invention.
Figure 2B:
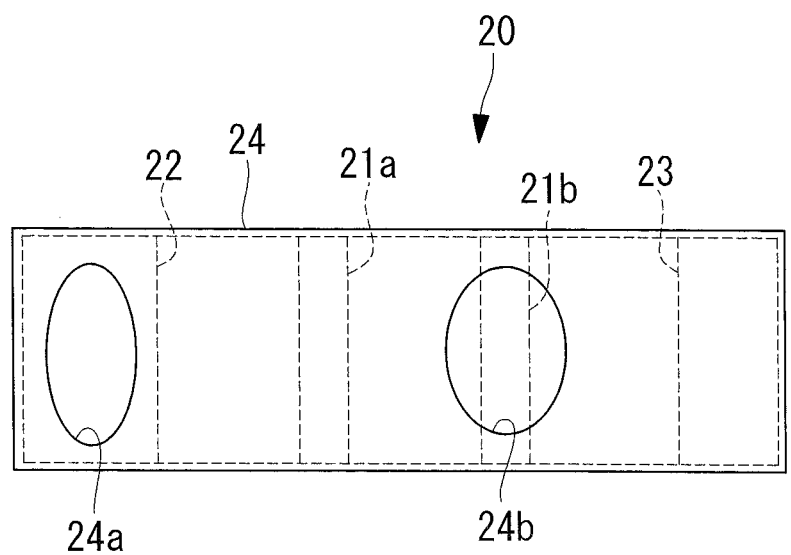
FIG. 2B is a diagram showing an external view of the immunochromatography device in FIG. 2A.

The pancreas testing kit according to this embodiment is provided with a collection vessel 1 in which a protease inhibitor A is retained in an outer cylinder 2 of a syringe, as shown in FIG. 1, and an immunochromatography device 20 that holds anti-SLOOP antibodies, as shown in FIGS. 2A and 2B.

The syringe of the collection vessel 1 is provided with the outer cylinder 2, a gasket 3 that is installed so as to be slidable in the outer cylinder 2 while dividing the internal space of this outer cylinder 2, and a plunger 4 that pushes and pulls the gasket 3. The protease inhibitor A is disposed in a space divided by the gasket 3 on the side closer to a suction port 2a. The suction port 2a is sealed by a cap 5 or the like.

The protease inhibitor A to be used is a water-soluble one that easily dissolves in pancreatic juice containing water as a main component and/or body fluid containing pancreatic juice. Examples of the protease inhibitor A that can suitably be used include phenylmethylsulfonyl fluoride (PMSF), amidinophenylmethanesulfonyl fluoride (APMSF), and 4-(2-aminoethyl)-benzenesulfonyl fluoride (AEBSF), which are sulfonyl-based compounds, 1-chloro-3-tosylamido-7-amino-2-heptanone hydrochloride (TLCK-HCL), which is a tosyl-based compound, aprotinin and leupeptin, which are peptide-based inhibitors, and so forth. These protease inhibitors A irreversibly inhibit mainly a serine protease and strongly inhibit proteases contained in the pancreatic juice in a large quantity, such as amylase, trypsin, elastase, and so forth.

Only one type of protease inhibitor A may be retained in the outer cylinder 2, or two or more types may be retained in the outer cylinder 2. In addition, the protease inhibitor A may be retained together with an inhibitor that inhibits the activity of other digestive enzymes, such as lipase and so forth.

The protease inhibitor A is freeze-dried powder. This makes it possible to dissolve the protease inhibitor A even more easily in the pancreatic juice and/or the body fluid containing pancreatic juice.

The amount of test fluid to be collected by using the collection vessel 1 is set to a predetermined amount in advance in accordance with the volume of the collection vessel 1 or the amount of test fluid required for a test. The weight of the protease inhibitor A to be retained in the outer cylinder 2 is determined so that a desired concentration value can be achieved when the protease inhibitor A is dissolved in the predetermined amount of test fluid to be collected.

As shown in FIG. 2A, the immunochromatography device 20 is provided with a support 21 on which the test fluid is spread, as well as a sampling pad 22 and an absorbing pad 23 that are disposed at the two ends of the support 21.

It suffices that the support 21 allows the test fluid to be spread thereon and, for example, a nitrocellulose membrane filter or the like is suitably used. The support 21 is provided with a strip-like labeling region 21a that holds a first antibody and a strip-like adsorptive region 21b in which a solid-phase second antibody is disposed at a position separated from the labeling region 21a. The first antibody and the second antibody are anti-S100P antibodies that recognize epitopes of S100P that are different from each other.

The first antibody is labeled with a substance having a predetermined color, such as a colloidal metal like colloidal gold, colloidal platinum, and so forth, or with colloidal latex (labeling substance) formed of synthetic latex, such as colored polystyrene latex or the like, or natural rubber latex and so forth.

The labeling substance for labeling the first antibody may be an enzyme, a radioactive substance, and so forth.

The sampling pad 22 is formed of a material having superior water absorbability, for example, a sheet or a film formed of a porous synthetic resin, such as porous polyethylene, porous polypropylene, and so forth, or cellulose paper, woven fabric, nonwoven fabric, and so forth, such as filter paper, cotton cloth, and so forth.

The absorbing pad 23 is formed of, among others, a material that can quickly absorb and hold fluid, for example, cotton cloth, filter paper, porous plastic nonwoven fabric formed of polyethylene, polypropylene, and so forth.

As shown in FIG. 2B, a plastic case 24 serves as external packaging for the support 21, sampling pad 22, and absorbing pad 23. In the case 24, a dropping window 24a is provided in the form of an opening at a position corresponding to the sampling pad 22 and an observation window 24b is provided in the form of an opening at a position corresponding to the adsorptive region 21b.

To use the thus-configured immunochromatography device 20, an operator drops the test fluid onto the sampling pad 22 from the dropping window 24a. The dropped test fluid spreads out over the support 21 by moving from the sampling pad 22 toward the absorbing pad 23. In the process of spreading, S100P contained in the test fluid forms a complex by bonding with the first antibody in the labeling region 21a. Subsequently, the complex is adsorbed at the adsorptive region 21b by bonding with the second antibody in the adsorptive region 21b. Then, a predetermined color develops in the adsorptive region 21b due to the accumulation of the complex in the adsorptive region 21b. Therefore, the operator can determine the presence/absence of S100P or measure the concentration thereof based on whether or not a band having the predetermined color appears in the observation window 24b or based on the shade of the band color.

Next, a method of detecting pancreatic disease using the thus-configured pancreas testing kit will be described.

With the method of detecting pancreatic disease according to this embodiment, duodenal juice containing pancreatic juice is collected in the collection vessel from the duodenum of a test subject, and the concentration of S100P in the collected duodenal juice containing pancreatic juice is measured by using the immunochromatography device 20. The collection method and the collection vessel for the duodenal juice are not limited to a catheter and a syringe that will be described as examples, so long as the pancreatic juice and/or body fluid containing pancreatic juice can be collected.

Figure 3:
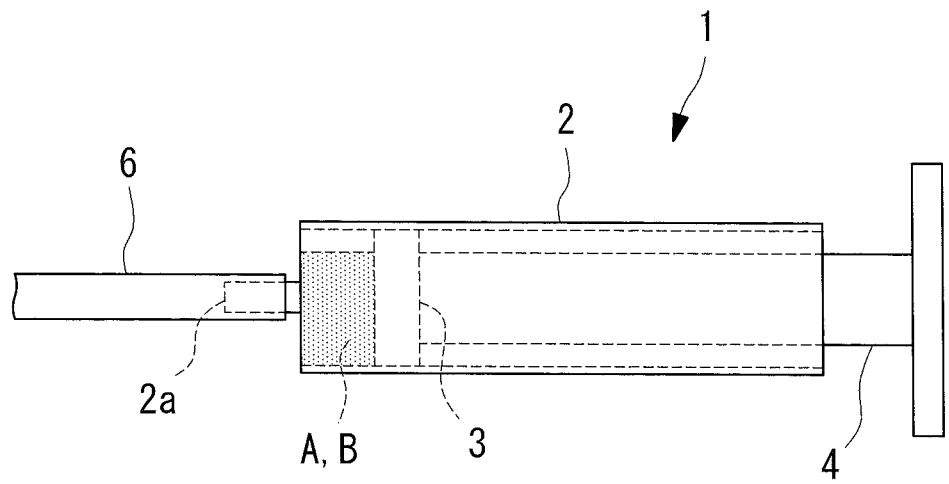
FIG. 3 is a diagram for explaining a method of using the collection vessel in FIG. 1.

Specifically, first, a catheter is disposed near a papilla in the duodenum via a channel in the endoscope inserted into the duodenum, the base end of the catheter 6 is connected to the suction port 2a of the outer cylinder 2, and the plunger 4 is pulled, as shown in FIG. 3. By doing so, the pancreatic juice secreted from the papilla into the duodenum is sucked and collected into the outer cylinder 2 in the form of the duodenal juice, together with bile and duodenum secretions.

Before sucking the duodenal juice, treatment may be performed to promote the secretion of pancreatic juice in the pancreas and the discharge of the pancreatic juice from the papilla into the duodenum; for example, a stimulant of pancreatic juice secretion, such as secretin or the like, may be administered to the test subject. By doing so, a sufficient amount of duodenal juice containing pancreatic juice can be used for the test. Alternatively, pancreatic juice discharged into the duodenum under physiological conditions and/or duodenal juice containing this pancreatic juice may be collected without applying such treatment. By doing so, it is possible to reduce the burden on the test subject associated with the tests.

After collecting the mixture of the pancreatic juice, the bile, and the duodenum secretions (hereinafter, referred to as "pancreatic juice/duodenal juice") into the outer cylinder 2 in the predetermined amount, the catheter 6 is removed from the suction port 2a, and the pancreatic juice/duodenal juice in the outer cylinder 2 is dropped into the dropping window 24a of the immunochromatography device 20 from the suction port 2a. Subsequently, the operator waits for, for example, 5 to 15 minutes, until the pancreatic juice/duodenal juice sufficiently spreads out over the support 21. With the procedure described above, the presence/absence of S100P in the pancreatic juice/duodenal juice, that is to say, the presence/absence of a pancreatic disease, such as pancreatic cancer, IPMN, or the like, can be tested based on whether or not a band appears in the observation window 24b. Note that the pancreas testing kit may include a dilution solution formed of a buffer solution or the like as an accessory, and the pancreatic juice/duodenal juice may be dropped into the dropping window 24a after diluting it with the dilution solution.

In the case in which the band is observed in the observation window 24b, the shade of the band color is visually measured or measured by using a reading device designed for immunochromatography, thus measuring the S100P concentration. The shade of the band color obtained in advance from pancreatic juice/duodenal juice of a healthy person may be used as a reference value, and the presence/absence of a pancreatic disease in the test subject may be judged by comparing this reference value and the measured shade of the band color. In this case, the reference value is set differently depending on whether pure pancreatic juice collected from a pancreatic duct is used or the pancreatic juice/duodenal juice is used, and, in addition, the setting also differs depending on the collected amount and time required for the collection, as well as whether or not a stimulant of pancreatic juice secretion is used. Therefore, reference values are required for the pancreatic juice and/or the body fluid containing pancreatic juice, serving as the test fluid, that are collected under different conditions.

In this case, with this embodiment, there is a strong correlation between the concentration of S100P contained in the pancreatic juice and/or the body fluid containing pancreatic juice and the presence/absence of a pancreatic disease, and when there is a pancreatic disease, the S100P concentration in the pancreatic juice and/or the body fluid containing pancreatic juice is increased at a high proportion. Therefore, it is possible to test the presence/absence of a pancreatic disease with high sensitivity.

Furthermore, the pancreatic juice/duodenal juice is quickly mixed with the protease inhibitor A in the outer cylinder 2 after flowing into the outer cylinder 2 from the catheter 6. By doing so, because degradation of S100P contained in the pancreatic juice/duodenal juice is quickly suppressed, it is possible to accurately measure the S100P concentration, and thus, it is possible to enhance the test sensitivity even more. Because the activity of protease in the pancreatic juice is particularly high compared with those in other digestive juices, the test precision can be effectively enhanced by setting the retained amount of the protease inhibitor A so that the concentration of the protease inhibitor A will be sufficiently high in the pancreatic juice/duodenal juice collected into the outer cylinder 2.

In addition, by collecting the pancreatic juice discharged into the duodenum in the form of the duodenal juice and using it in the test, the pancreatic juice can be collected in a simple manner while reducing invasiveness as compared with the case in which pure pancreatic juice in a pancreatic duct is collected by inserting the catheter 6 into the pancreatic duct. In addition, because the operation of the immunochromatography device 20 does not require special equipment nor is it time consuming, it is possible to perform a high-sensitivity test at low cost and in a short period of time even at, for example, a regularly visited, relatively small hospital or the like.

Note that, in this embodiment, although the pancreatic juice that is discharged into the duodenum from the papilla, which is mixed with the bile and the duodenum secretions, is used for the test, alternatively, pure pancreatic juice collected from the pancreatic duct may be used for the test. The pure pancreatic juice can be collected by sucking it with the catheter inserted into the pancreatic duct from the papilla while imaging the site or by disposing a balloon catheter or a tube in the pancreatic duct for a certain amount of time.

By doing so, because the pure pancreatic juice collected from the pancreatic duct is not diluted with the duodenal juice, it is possible to more accurately measure the S100P concentration in the test subject.

In addition, in this embodiment, although an inhibitor in the form of freeze-dried powder is used as the protease inhibitor A, alternatively, an inhibitor in the form of a fluid, dissolved in a buffer solution or the like, may be used. By doing so, even if the collected amount of the pancreatic juice/duodenal juice is low, the protease inhibitor A can easily and evenly be mixed with the pancreatic juice/duodenal juice.

In addition, in this embodiment, although the configuration in which a syringe is used as the collection vessel 1 has been described as an example, the configuration of the collection vessel 1 is not limited thereto, and any configuration is permissible so long as the pancreatic juice and/or the body fluid containing pancreatic juice can be sucked in via the catheter connected to the collection vessel, and the collection vessel can retain a protease inhibitor that inhibits the activity of the protease contained in the pancreatic juice by coming into contact with the pancreatic juice and/or the body fluid containing pancreatic juice. For example, as shown in FIG. 4, a trap-type vessel may be used as the collection vessel 1, or, as shown in FIG. 5, a vessel whose interior is in a vacuum state may be used.

Figure 4:
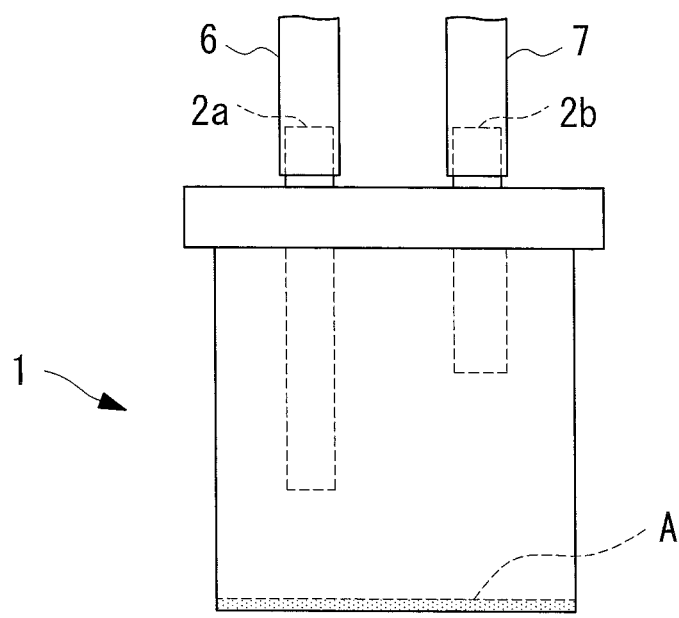
FIG. 4 is a diagram showing a modification of the collection vessel in FIG. 1.
Figure 5:
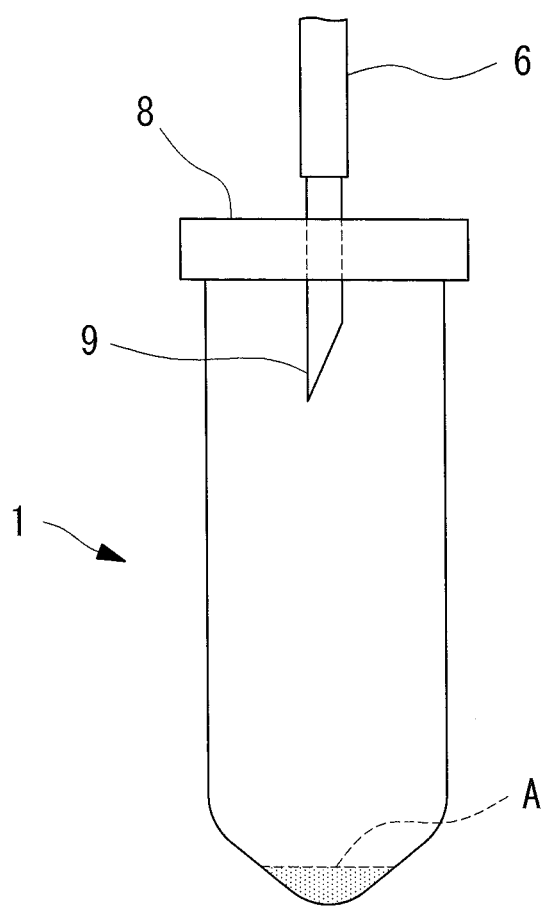
FIG. 5 is a diagram showing another modification of the collection vessel in FIG. 1.

In addition, it suffices that the collection vessel be configured such that the collected pancreatic juice and/or body fluid containing pancreatic juice quickly come into contact with the protease inhibitor A retained in the vessel in advance, and it is possible to employ a collection vessel other than the collection vessels 1 shown as examples in FIGS. 1, 4, and 5. In addition, a collection means other than the use of the catheter described as an example may be employed, and the pancreatic juice and/or the body fluid containing pancreatic juice may be collected by means of, for example, suction, absorption, recovery, and so forth. The configuration of the collection vessel can be selected in accordance with the collection means.

The collection vessel 1 shown in FIG. 4 is provided with a suction port 2a that is connected to the catheter 6 and an exhaust port 2b that is connected to a tube 7 connected to an exhaust pump or the like, and, by exhausting air from the exhaust port 2b, the pancreatic juice/duodenal juice flows in from the suction port 2b and accumulates in the collection vessel 1.

With the collection vessel 1 shown in FIG. 5, an opening is sealed by a stopper 8 formed of an elastic member, for example, rubber or the like, and the pancreatic juice/duodenal juice is sucked into the interior thereof by penetrating the stopper 8 with a hollow needle 9 connected to the catheter 6.

In this way also, the activity of the protease contained in the pancreatic juice and/or the body fluid containing pancreatic juice can quickly be inhibited after collection, and thus, the test precision of S100P contained in the collected pancreatic juice can be enhanced.

Here, in the case of a conventional collection vessel for body fluid, the collection vessel is connected to the base end of a catheter and the pancreatic juice and/or the body fluid containing pancreatic juice are sucked in and accumulated therein, and, after completing the suction, the pancreatic juice and/or body fluid containing pancreatic juice are dispensed to add a protease inhibitor thereto; therefore, there is a problem in that protein degradation also advances in the collection vessel during the suction, and thus, it is difficult to obtain an accurate test result from the collected pancreatic juice and/or body fluid containing pancreatic juice.

In contrast, with the collection vessel 1 according to this embodiment, by quickly suppressing the activity of protease contained in the collected pancreatic juice and/or body fluid containing pancreatic juice, the detection precision can be enhanced not only for S100P but also for other proteins contained in the pancreatic juice and/or the body fluid containing pancreatic juice, and thus, the collection vessel 1 can also effectively be used for a pancreas test in which other proteins serve as markers.

In addition, in this embodiment, although the S100P concentration is measured by means of the immunochromatography method, other measurement methods may be used so long as measurements can be taken in a simple manner by using a solid-phase antibody. The measurement can be taken by using, for example, a small surface plasmon resonance device (SPR), microfluidisc, or the like.

EXAMPLES

Next, Examples of the method of detecting pancreatic disease according to the above-described embodiment will be described.

Example 1

The test sensitivity of the method of detecting pancreatic disease according to the present invention was assessed by the following experiment.

Pancreatic juice and body fluid containing pancreatic juice which served as test fluids, were collected by means of catheter suction from test subjects including 31 patients serving as a pancreatic cancer patient group and 7 patients serving as an IPMN patient group. The test fluids collected from the patients were quickly frozen and stored after collection, and, subsequently, the concentrations of S100P contained in the individual test fluids were measured by using an ELISA kit made by CycLex Co., Ltd. By using the same methods, the test fluids were collected and measurements were taken therefrom also for 6 benign pancreatic cyst patients (MCN, SCN), serving as a control group. Diseases of the individual patients were diagnosed by means of pathological diagnosis.

The pure pancreatic juice collected from the pancreatic duct and the pancreatic juice/duodenal juice were used as the test fluids. Regarding the pancreatic juice/duodenal juice, duodenal juice containing pancreatic juice that is physiologically secreted and discharged (hereinafter, referred to as "pancreatic juice/duodenal juice (−)"), as well as duodenal juice collected after promoting the secretion of pancreatic juice by means of secretin administration (hereinafter, referred to as "pancreatic juice/duodenal juice (+)") were used. Furthermore, regarding the pancreatic juice/duodenal juice (−) and (+), measurements were taken from those collected by using a collection vessel retaining a protease inhibitor (inhibitor (+)) and an empty collection vessel (inhibitor (−)). Measurement results are shown in FIGS. 6 and 7.

Figure 6:
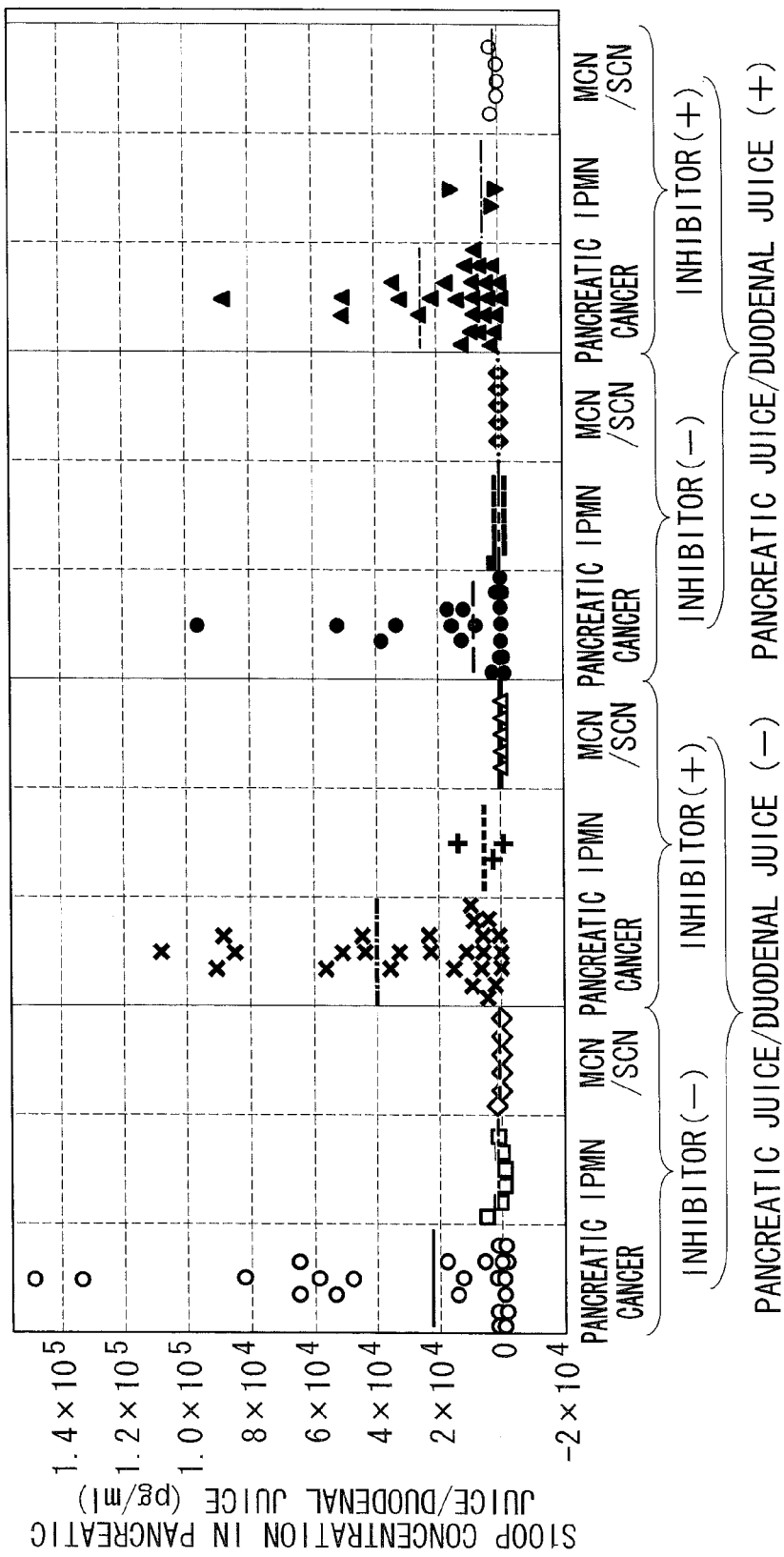
FIG. 6 is a graph showing the result obtained by measuring the S100P concentrations in pancreatic juice and duodenal juice in Example 1.
Figure 7:
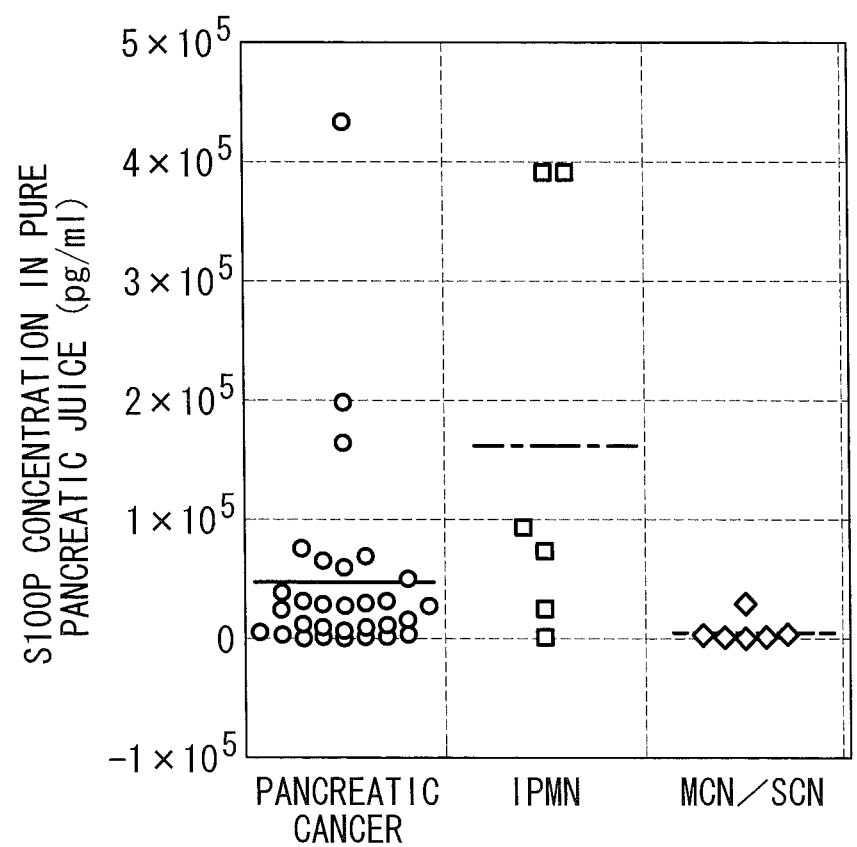
FIG. 7 is a graph showing the result obtained by measuring the S100P concentration in pure pancreatic juice in Example 1.

In FIGS. 6 and 7, the horizontal axis shows example diseases of the patients, and the vertical axis shows the S100P concentration in the pure pancreatic juice or the duodenal juice. Individual dots show the S100P concentrations in the pancreatic juice or the duodenal juice collected from the individual patients under the above-described conditions.

Next, the highest value of the S100P concentrations obtained from the control group was used as a cut-off value, and, when a S100P concentration obtained from a pancreatic cancer patient or an IPMN patient exceeded this cut-off value, this patient was judged to be positive in the pancreatic cancer or IPMN test. Then, for the respective test conditions, positive rates were calculated as proportions of the patients judged to be positive relative to the total number of patients whose tests were successfully completed, among the thirty-one patients in pancreatic cancer patient group, as well as the seven patients in the IPMN patient group. The results are shown in Table 1. Data for test fluids that were not successfully collected under the above-described conditions were excluded from the statistics shown in Table 1, FIG. 6, and FIG. 7.

As is clear from Table 1, high positive rates were obtained under all test conditions. In other words, it is possible to test with high sensitivity the presence/absence of pancreatic cancer or IPMN by measuring the concentrations of S100P contained in pancreatic juice/duodenal juice or pure pancreatic juice, thus confirming the effectiveness of the method of detecting pancreatic disease of the present invention in the tests of pancreatic cancer or IPMN.

In addition, in the tests using the pancreatic juice/duodenal juice, it was confirmed that the test sensitivity can be increased considerably by using the collection vessel according to the present invention containing the protease inhibitor. Specifically, it was confirmed that, by inhibiting the degradation of S100P due to a large amount of protease secreted together with the pancreatic juice, the collection vessel containing the protease inhibitor is particularly effective in tests in which secretion is promoted.

Example 2

Next, an immunochromatography device according to this Example was fabricated by using the two types of anti-S100P antibodies (made by MBL Co., Ltd.) used for ELISA employed in Example 1 as the first antibody and the second antibody. By using this immunochromatography device to test the test fluids used in Example 1, the correlation between test results respectively obtained by means of the ELISA method and the immunochromatography method was checked.

The immunochromatography device according to this Example was fabricated by fabricating the support by using a nitrocellulose film, and labeling the first antibody with colloidal gold. Then, the test fluids used in Example 1 were tested by using the fabricated immunochromatography device, and the presence/absence of band color was determined and the shade of the color was measured.

When the measured shades of the color in the immunochromatography device were divided into three classes, it was confirmed that there was a correlation with the concentrations quantified by the ELISA method. The amount of time required for the test of this Example was about 15 minutes. In other words, it was confirmed that, by using the immunochromatography method, a test result with sufficiently high sensitivity can be obtained in a short period of time.

Example 3

Based on the results in Example 1, by using the method in which the protease inhibitor is retained in the collection vessel in advance and the secretin administration for promoting secretion is not performed, the pancreatic juice/duodenal juice was collected and the S100P concentrations were measured for 41 pancreatic cancer patients, 17 IPMN patients, 6 benign pancreatic cyst (SCN, MCN) patients, 4 chronic pan-

TABLE 1

| TEST FLUID | PROTEASE INHIBITOR | SECRETION PROMOTION | CUT-OFF VALUE (pg/ml) | POSITIVE RATE (%) | |
| --- | --- | --- | --- | --- | --- |
| | | | | PANCREATIC CANCER | IPMN |
| PURE PANCREATIC JUICE | | YES | 3000 | 77 (23/30) | 86 (23/30) |
| PANCREATIC JUICE/ DUODENAL JUICE | NO | NO | 1000 | 55 (17/31) | 57 (4/7) |
| | | YES | 500 | 39 (12/31) | 17 (1/6) |
| | YES | NO | 500 | 93 (25/27) | 67 (2/3) |
| | | YES | 500 | 81 (22/27) | 33 (1/3) | creatitis patients, and 3 pancreatic endocrine tumor patients. The collection of the pancreatic juice/duodenal juice and the measurement of the S100P concentration were performed by using the same method as in Example 1. The measurement results are shown in FIG. 8. In FIG. 8, the vertical axis is on a logarithmic scale.

The highest value among the measured values of the S100P concentrations obtained from the six benign pancreatic cyst patients was set as the cut-off value, and the positive rates were calculated for the respective example diseases. As a result, the positive rates of the pancreatic diseases were 90% for pancreatic cancer, 90% for IPMN, 100% for chronic pancreatitis, and 100% for pancreatic endocrine tumor.

Based on the above-described experimental results, it was confirmed that various pancreatic diseases described above can be detected with high sensitivity by measuring the S100P concentration in duodenal juice containing pancreatic juice.

REFERENCE SIGNS LIST 1 collection vessel
2 outer cylinder
2a suction port
2b exhaust port
3 gasket
4 plunger
5 cap
6 catheter
7 tube
8 stopper
9 hollow needle
20 immunochromatography device
21 support
21a labeling region (first antibody, anti-SLOOP antibody)
22b adsorptive region (second antibody, anti-S100P antibody)
22 sampling pad
23 absorbing pad
24 case
24a dropping window
24b observation window
A protease inhibitor
B pancreatic juice

The invention claimed is:

1. A method of detecting pancreatic disease, comprising:
    detecting a concentration of S100P in at least one of a pancreatic juice and a body fluid containing pancreatic juice collected from a test subject by using a solid-phase antibody; and
    detecting the pancreatic disease based on the detected concentration of S100P, wherein the at least one of the pancreatic juice and the body fluid containing pancreatic juice is contacted with a protease inhibitor that inhibits an activity of a protease contained in the pancreatic juice, and wherein the pancreatic juice and the body fluid containing pancreatic juice are obtained without administering a stimulant of pancreatic juice secretion.

2. The method of detecting pancreatic disease according to claim 1, wherein the pancreatic juice is collected from a pancreatic duct.

3. The method of detecting pancreatic disease according to claim 1, wherein the body fluid containing pancreatic juice is collected from a duodenum.

4. The method of detecting pancreatic disease according to claim 3, wherein the body fluid containing pancreatic juice is a duodenal juice.

5. The method of detecting pancreatic disease according to claim 1, wherein the concentration of S100P is measured by immunochromatography using the solid-phase antibody.

6. The method of detecting pancreatic disease according to claim 1, wherein the concentration of S100P is detected with a fist antibody and a second antibody, wherein the first antibody is different than the second antibody.

* * * * *